(12) United States Patent
Broell

(10) Patent No.: US 7,342,054 B2
(45) Date of Patent: Mar. 11, 2008

(54) METHOD FOR PRODUCING POLYMERISABLE POLYHYDROXY COMPOUNDS

(75) Inventor: Dirk Broell, Langen (DE)

(73) Assignee: Roehm GmbH & Co. KG, Darmstadt (DE)

( * ) Notice: Subject to any disclaimer, the term of this patent is extended or adjusted under 35 U.S.C. 154(b) by 77 days.

(21) Appl. No.: 10/567,361

(22) PCT Filed: Jul. 22, 2004

(86) PCT No.: PCT/EP2004/008182

§ 371 (c)(1),
(2), (4) Date: Feb. 6, 2006

(87) PCT Pub. No.: WO2005/047227

PCT Pub. Date: May 26, 2005

(65) Prior Publication Data

US 2006/0258830 A1    Nov. 16, 2006

(30) Foreign Application Priority Data

Oct. 24, 2003    (DE) ............... 103 49 972

(51) Int. Cl.
*C08L 33/10*    (2006.01)
*C07C 69/52*    (2006.01)
(52) U.S. Cl. ..................... 523/106; 560/224
(58) Field of Classification Search ............ None
See application file for complete search history.

(56) References Cited

FOREIGN PATENT DOCUMENTS

| WO | 90/07547 | 7/1990 |
|---|---|---|
| WO | 00/63149 | 10/2000 |
| WO | 00/63150 | 10/2000 |

*Primary Examiner*—Paul A. Zucker
(74) *Attorney, Agent, or Firm*—Oblon, Spivak, McClelland, Maier & Neustadt, P.C.

(57) ABSTRACT

The invention relates to a method for producing glycerol monomethacrylate (GMMA).

10 Claims, 1 Drawing Sheet

METHOD FOR PRODUCING POLYMERISABLE POLYHYDROXY COMPOUNDS

The invention relates to a process for preparing substituted esters of (meth)acrylic acid which have a plurality of hydroxyl groups in the ester group.

STATE OF THE ART

Beinert, Hild and Rempp (Die Makromolekulare Chemie, 175, 2069-2077 (1974)) describe the preparation of (2,2-dimethyl-1,3-dioxolan-4-yl)methyl methacrylate by reacting a mixture which comprises methacrylic acid and thionyl chloride in a solvent mixture composed of hexamethylenephosphoramide (HMPA) and diethyl ether with 2,3-O-isopropylideneglycerol. The resulting methacrylate is polymerized anionically. In a polymer-like reaction, the polymer is converted to poly(2,3-dihydroxypropyl methacrylate).

The monomer is prepared at from −5° C. to 15° C. in a toxicologically controversial solvent. Owing to the toxicological problems, this process cannot be employed in industrial technology.

WO 00/63149 (Hydron Ltd.) describes a process for preparing a polymerizable diol by reacting a protected glycerol derivative of methacrylic acid with an immobilized acid in the form of an acidic ion exchanger. The acetone which forms is blown out of the reaction system with air.

The reaction vessel is initially charged with (2,2-dimethyl-1,3-dioxolan-4-yl)methyl methacrylate, deionized water and the washed cation exchanger. Subsequently, an air stream which ensures the mixing of the reaction mixture is passed through the mixture for 48 h.

After the end of the reaction, the ion exchanger is filtered off and excess water is discharged by means of a stream of dried air.

The process of WO 00/63149 has several disadvantages:

The blowing of the air stream into the reaction mixture results in the ion exchanger experiencing increased attrition. In the event of higher demands on the purity of the product, the attritus, which cannot be removed completely even by filtration, is not acceptable.

The method of reducing the water content of the product by blowing through dried air leads to unacceptable yield losses. The publication does not state that any kind of measures for reducing the product losses might have been taken.

For some applications, the water content is too high. The disclosure does not describe any methods of reliably and reproducibly setting the water content.

WO 00/63150 (Hydron Ltd.) likewise describes a process for preparing a polymerizable diol by the ion exchanger-catalyzed reaction of a protected glycerol derivative of methacrylic acid with elimination of acetone. The methacrylic acid which is inevitably formed as a by-product is scavenged with a basic ion exchanger in a second step.

This process too has the following disadvantages:

As a result of using the ion exchanger twice, the content of attritus in the product increases.

The water content of the product is adjusted to <3% by passing through dried air. This method is associated with yield losses.

The content of crosslinker (glyceryl methacrylate) is 0.8%.

Object

In view of the above-discussed state of the art, the objects are thus to provide a process for preparing glyceryl monomethacrylate (GMMA) which no longer has the disadvantages present in the state of the art and in particular thermally stresses the reaction mixture as little as possible, possesses a defined, minimum water content of the product, prevents the troublesome attrition of the ion exchanger without extensive measures, constitutes a semicontinuous process instead of a batch process, does not require as much as the amount of the stabilizer customary in the state of the art, gives rise to a storage-stable product which discolors only insignificantly if at all, manages with nontoxic polymerization stabilizer in the product.

Moreover, as a result of the increased thermal stress, crosslinking compounds are formed in the monomer and polymerize actually in the monomer and lead to an undesired viscosity increase which makes the monomer unsaleable. Furthermore, even relatively small contents of crosslinkers in the monomer lead to changes in properties in the polymer, which are likewise undesired. The increased thermal stress during the preparation process should therefore be kept to a minimum.

Figure 1:
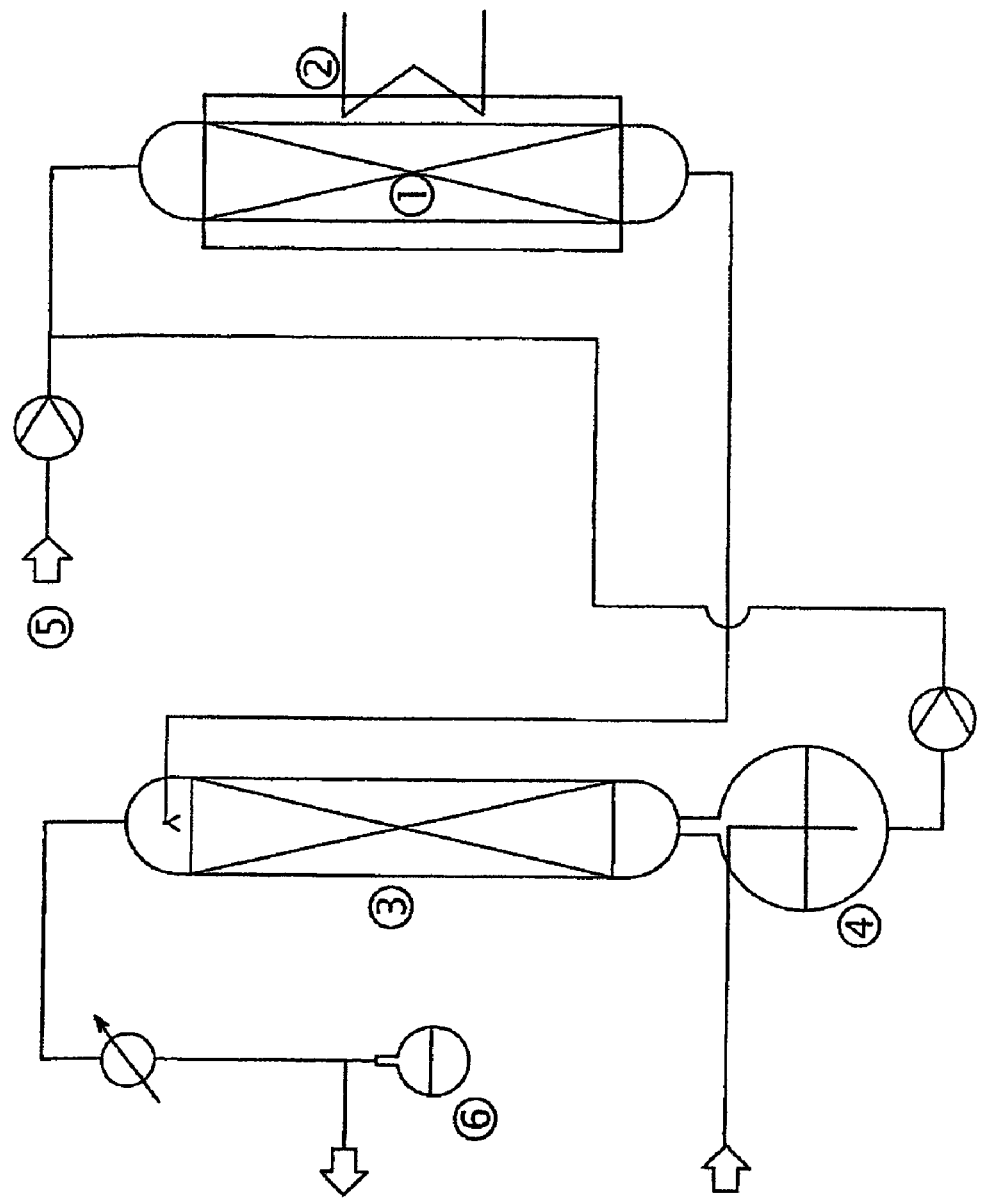
FIG. 1 is a flow diagram of a system for carrying out the process of the present invention.

This object is achieved by a process for preparing compounds of the formula I

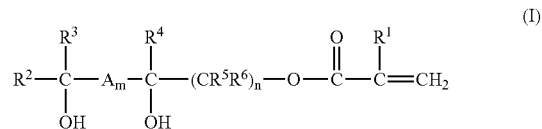

where $R^1$=H or $CH_3$ $A=(CH_2)$ where m may assume the values of 0 or 1, $R^{2-6}$ =may be the same or different and assume the definitions of OH, H, aliphatic or aromatic hydrocarbon, for example methyl, ethyl, propyl, isopropyl, butyl, isobutyl, tert-butyl, pentyl, hexyl, cyclopentyl, cyclohexyl, methylcyclohexyl, isobornyl, heptyl, octyl, substituted hydrocarbon radicals, for example hydroxyethyl, 2-(N,N-di-methylamino)ethyl, 2-(N,N-dimethyl-amino)propyl, 2-hydroxypropyl, 2-hydroxyethyl, 2-ethylhexyl, isooctyl, n may assume the values of 0, 1 or 2, characterized in that compounds of the formula II

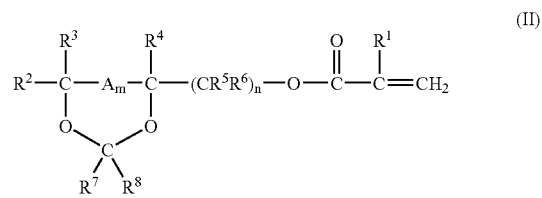

where $R^1$, $R^2$, $R^3$, $R^4$, $R^5$, $R^6$, A, m and n are each as defined above and $R^7$ and $R^8$ may be the same or different and may assume the definitions of methyl, ethyl or propyl are reacted with water in small amounts over an acidic ion exchanger in a fixed bed, and the resulting compound III

$$R^7R^8C=O \quad (III)$$

is removed continuously from the reaction medium, and the product is stabilized against polymerization and discoloration with tocopherol derivatives. A favorable ratio of compound II to water is between 1:1 and 1:3. Very good results are achieved at a ratio of 1:1.1 and 1:2.5.

A particular embodiment of the invention envisages the use at a ratio of from 1:1.2 to 1:2. A very particularly appropriate ratio is found to be 1:1.5. In all of the above data, the water content present in the ion exchanger is also taken into account.

In the context of the invention, preference is given to using a tocopherol compound for the storage and color stabilization of ethylenically unsaturated monomers.

The tocopherol compounds which can be used in the context of the invention are chroman-6-ols (3,4-dihydro-2H-1-benzopyran-6-ols) 2-substituted by a 4,8,12-trimethyltridecyl radical. The tocopherols which can be used with preference in accordance with the invention include alpha-tocopherol, beta-tocopherol, gamma-tocopherol, delta-tocopherol, zeta2-tocopherol and eta-tocopherol, all of the aforementioned compounds in each case in the (2R, 4'R, 8'R) form, and also alpha-tocopherol in the (all-rac) form. Preference is given to alpha-tocopherol in the (2R, 4'R, 8'R) form (trivial name: RRR-alpha-tocopherol) and the synthetic racemic alpha-tocopherol (all-rac-alpha-tocopherol). Of these, the latter is in turn of particular interest owing to the relatively low cost.

The amount of tocopherol compound which can be employed for storage and color stabilization of base-stabilized monomers may differ over a wide range according to the monomer and the desired efficiency. For many fields of use, amounts of up to 1000 ppm based on the monomer mass are sufficient. Frequently, even very small added amounts of 10 ppm are sufficient in order to achieve noticeable improvement in the storage and color stabilization. Should fewer than 10 ppm be used, significant storage and color stabilization is generally not, however, perceptible. A favorable range for the amount to be added is therefore between 10 and 1000 ppm of tocopherol compound based on the monomer mass. Very good results are achieved in the addition range from 50 to 800 ppm. A particular embodiment of the invention envisages the use in an amount of from 100 to 600 ppm. Very particularly appropriately, about 500 ppm of tocopherol compound are used.

The notation (meth)acrylic encompasses methacrylic, acrylic and mixtures of the two.

Process Description

The hydrolysis of isopropylideneglyceryl methacrylate (IPGMA) to glyceryl monomethacrylate (GMMA) was investigated in a laboratory system. The flow diagram of the system can be seen in FIG. 1.

Charge: the bottom (4) of a separating column (3) is charged with 500 g of IPGMA which is base-stabilized with hydroquinone monomethyl ether.

Base stabilization is understood to mean the stabilization, generally customary in (meth)acrylate chemistry, of monomers or monomer mixtures with hydroquinones, for example hydroquinone monomethyl ether, 4-methyl-2,6-di-tert-butylphenol, 2,4-dimethyl-6-tert-butylphenol, phenothiazine, N-nitrosophenyl-hydroxylamine, diethylhydroxylamine, 2,6-di-tert-butyl-alpha-(dimethylamino)-p-cresol or 4-hydroxy-2,2,6,6-tetramethylpiperidine 1-oxyl (rad.) (e.g. TEMPOL®) or of mixtures of the aforementioned compounds. For each individual substance, the amount of stabilizer used is, for example, 35 ppm. The base stabilization is added before the reaction. In the case that the monomers are admixed with the above-described base stabilization, the amount of tocopherol added as storage stabilizer after the reaction is 10-1000 ppm based on the amount of monomer.

Without base stabilization of the monomers, the amount of tocopherol added as storage stabilizer after the reaction is 100-600 ppm.

Pre-reaction: at the start of the experiment, the bottom contents are pumped under ambient pressure with the aid of a gear pump from the top onto a temperature-controlled (40° C.) water-moist ion exchanger fixed bed (for example from Dow Chemical, type: Dowex M-31) (1, 2). The water present in the ion exchanger reacts with IPGMA to form GMMA and acetone. The reaction mixture subsequently passes through a separating column—acetone is distilled out of the reaction mixture herein (6)—back into the bottom, whence it is pumped again to the fixed bed (circulation mode).

Main reaction: after a certain time (approx. 30 min), a certain amount of water (approx. 45 g) is metered in directly upstream of the fixed bed (5) with the aid of a pump within a certain time interval (approx. 1 h). At the same time, the pressure in the reaction circulation system is lowered to approx. 150 mbar in order to remove acetone as fully as possible.

Post-reaction: subsequently, the pressure is reduced stepwise further to approx. 20 mbar in order to remove residual amounts of acetone and excess water. After a certain time interval (approx. 2 h), the plant is shut down and the finished reaction product is discharged from bottom and fixed bed.

| Reference numeral list | |
|---|---|
| No. | Designation |
| 1 | ion exchanger |
| 2 | heating jacket |
| 3 | separating column |
| 4 | bottom |
| 5 | water feed |
| 6 | acetone/water distillate |

The table shows the results of the turbidity measurement.

The turbidity measurements are carried out with the Hach 2100AN laboratory turbidimeter. It measures turbidities of from 0 to 10 000 NTU (nephelometric turbidity units; corresponds by definition to formazin turbidity units=TE/F). The turbidimeter corresponds to the standard EN 270 27 (ISO 7027). The formazin standard is defined in the 13th edition (1971) of Standard Methods of the Examination of Water and Wastewater, published by AWWA (American Waterworks Association).

The sample to be analyzed is charged into the analytical cuvette. This is subsequently rubbed with a lint-free cloth and a thin film of silicone oil is applied externally. After the filter module has been inserted into the turbidimeter, the cuvette is inserted and the turbidity value is determined.

| Stabilization | | Storage | Turbidity in NTU | | | | |
|---|---|---|---|---|---|---|---|
| HQME [ppm] | Tocopherol [ppm] | temperature. in ° C. | 0 d | 7 d (1 wk.) | 14 d (2 wk.) | 21 d (3 wk.) | 28 d (1 mth.) |
| 33 | 0 | 30 | 1 | 1.6 | 1.6 | 1.7 | 5.3 |
| 33 | 100 | 30 | 1 | 1.1 | 0.7 | 0.8 | 1.2 |

HQME = hydroquinone monomethyl ether

What is claimed is:

1. A process for preparing a compound of formula I

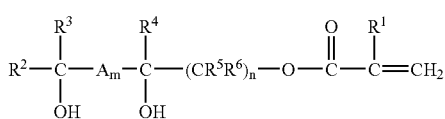 (I)

where
R$^1$ is H or CH$_3$
A is (CH$_2$) where m has the values of 0 or 1,
R$^{2-6}$ are the same or different and are OH, H, aliphatic or aromatic hydrocarbon,
n has the values of 0, 1 or 2,
comprising reacting
a compound of the formula II

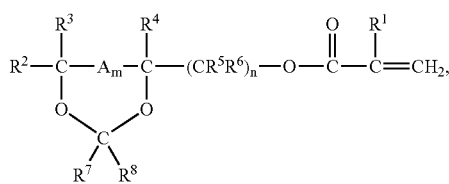 (II)

where R$^1$, R$^2$, R$^3$, R$^4$, R$^5$, R$^6$, A, m and n are each as defined above and R$^7$ and R$^8$ may be the same or different and are methyl, ethyl or propyl, with water in amounts wherein the ratio of compound (II) to water is between 1:1 and 1:3 over an acidic ion exchanger in a fixed bed, and the resulting compound III $$R^7R^8C=O \qquad (III)$$

is removed continuously from the reaction medium, and wherein no dried air is blown into the reaction medium to remove water or compound (III) therefrom, and wherein compound III is removed by reduction in pressure.

2. The process as claimed in claim 1, wherein stabilization against polymerization and discoloration is effected with tocopherol derivatives.

3. The process as claimed in claim 1, wherein stabilization against polymerization and discoloration is effected with tocopherol in an amount of 10 ppm-1000 ppm based on the monomer mixture.

4. A method for producing a contact lens comprising utilizing the compound of Formula I produced by the process as claimed in claim 1 to produce the contact lens.

5. A method for producing a water-soluble polymer comprising utilizing the compound of Formula I produced by the process as claimed in claim 1 to produce the water-soluble polymer.

6. The process as claimed in claim 1, wherein R$^{2-6}$ are the same or different and are methyl, ethyl, propyl or isopropyl.

7. The process as claimed in claim 1, wherein the ratio of compound (II) to water is between 1:1.1 and 1:2.5.

8. The process as claimed in claim 1, wherein the ratio of compound (II) to water is between 1:1.2 and 1:2.

9. The process as claimed in claim 1, wherein a pre-reaction is carried out between compound II and water present in the acidic ion exchanger, whereby a reaction mixture comprising compound I and compound III is formed.

10. The process as claimed in claim 9, wherein following the pre-reaction, the reaction mixture subsequently passes through a separating column, wherein compound III is distilled out of the reaction mixture and recycled to the fixed bed.

* * * * *